United States Patent
Dagum

(10) Patent No.: US 9,474,481 B2
(45) Date of Patent: *Oct. 25, 2016

(54) METHOD AND SYSTEM FOR ASSESSMENT OF COGNITIVE FUNCTION BASED ON ELECTRONIC DEVICE USAGE

(71) Applicant: Mindstrong, LLC, Los Altos Hills, CA (US)

(72) Inventor: Paul Dagum, Los Altos Hills, CA (US)

(73) Assignee: MINDSTRONG, LLC, Los Altos Hills, CA (US)

( * ) Notice: Subject to any disclaimer, the term of this patent is extended or adjusted under 35 U.S.C. 154(b) by 320 days.

This patent is subject to a terminal disclaimer.

(21) Appl. No.: 14/462,142

(22) Filed: Aug. 18, 2014

(65) Prior Publication Data

US 2015/0112899 A1   Apr. 23, 2015

Related U.S. Application Data

(63) Continuation-in-part of application No. 14/059,682, filed on Oct. 22, 2013, now Pat. No. 9,420,970.

(51) Int. Cl.
*G06N 5/02*  (2006.01)
*A61B 5/16*  (2006.01)
(Continued)

(52) U.S. Cl.
CPC ............ *A61B 5/16* (2013.01); *A61B 5/6898* (2013.01); *G06F 19/345* (2013.01); *G06F 19/3406* (2013.01); *G06F 19/3418* (2013.01); *G06N 5/022* (2013.01); *A61B 5/0022* (2013.01); *A61B 5/01* (2013.01); *A61B 5/024* (2013.01); *A61B 5/0476* (2013.01); *A61B 5/1112* (2013.01);
(Continued)

(58) Field of Classification Search
None
See application file for complete search history.

(56) References Cited

U.S. PATENT DOCUMENTS 7,837,472 B1 *  11/2010  Elsmore .............. G06F 19/3487
                                                   434/236
8,527,213 B2 *  9/2013   Kailas ...................... A61B 5/01
                                                   702/19

(Continued)

OTHER PUBLICATIONS

International Search Report and Written Opinion for PCT/US14/52227 dated Nov. 25, 2014.

(Continued)

*Primary Examiner* — Stanley K Hill
*Assistant Examiner* — Mikayla Chubb
(74) *Attorney, Agent, or Firm* — King & Spalding LLP

(57) ABSTRACT

A system and method that enables a person to unobtrusively quantify the effect of mobility, physical activity, learning, social interaction and diet on cognitive function. The method records on the electronic device one of global positioning system longitude and latitude coordinates, accelerometer coordinates, and gyroscope coordinates, one of outgoing and incoming phone calls, outgoing and incoming emails, and outgoing and incoming text messages, one of URLs visited on an internet browser application, books read on an e-reader application, games played on game applications, and the nutritional content of food consumed, performs the step of learning a function mapping from those recordings to measurements of cognitive function using a loss function to identify a set of optimal weights that produce a minimum for the loss function, uses those optimal weights to create the function mapping, and performs the step of computing the variance of the cognitive function measurements that is explained by the function mapping to assign an attribution to the effect of physical activity on measured changes in cognitive function.

19 Claims, 11 Drawing Sheets

(51) Int. Cl.
*A61B 5/00* (2006.01)
*G06F 19/00* (2011.01)
*A61B 5/01* (2006.01)
*A61B 5/024* (2006.01)
*A61B 5/0476* (2006.01)
*A61B 5/11* (2006.01)
*A61B 5/145* (2006.01)
*G06N 3/04* (2006.01)

(52) U.S. Cl.
CPC ............ *A61B5/1118* (2013.01); *A61B 5/1123* (2013.01); *A61B 5/14542* (2013.01); *A61B 5/7267* (2013.01); *G06N 3/0454* (2013.01)

(56) References Cited

U.S. PATENT DOCUMENTS

| | | | | |
|---|---|---|---|---|
| 2008/0229408 A1* | 9/2008 | Dinges | ............... | G06K 9/00885 726/19 |
| 2008/0242952 A1* | 10/2008 | Jung | ...................... | A61B 5/411 600/300 |
| 2011/0230781 A1* | 9/2011 | Lee | ........................ | A61B 5/048 600/544 |
| 2012/0150545 A1* | 6/2012 | Simon | .................. | A61B 5/0476 704/270 |
| 2013/0179472 A1* | 7/2013 | Junqua | .............. | G06F 17/30292 707/796 |
| 2014/0075464 A1* | 3/2014 | McCrea | .............. | G06F 19/3418 725/14 |
| 2014/0081100 A1* | 3/2014 | Muhsin | ................ | A61B 5/0002 600/324 |
| 2014/0107494 A1* | 4/2014 | Kato | ..................... | A61B 5/7267 600/473 |
| 2014/0114889 A1 | 4/2014 | Dagum | | |
| 2014/0121559 A1* | 5/2014 | Stevens | .................... | A61B 5/16 600/558 |
| 2014/0172467 A1* | 6/2014 | He | ........................ | B60K 28/066 705/4 |
| 2015/0279226 A1* | 10/2015 | Harrison | .................. | G09B 7/04 434/353 |
| 2015/0279227 A1* | 10/2015 | Huber | ...................... | G09B 7/02 434/353 |
| 2016/0022193 A1* | 1/2016 | Rau | ........................ | A61B 5/165 600/301 |
| 2016/0220598 A1* | 8/2016 | McGavern | ......... | A61K 31/7076 514/17.8 |

OTHER PUBLICATIONS

International Search Report and Written Opinion for PCT/US14/52222 dated Dec. 2, 2014.

* cited by examiner

METHOD AND SYSTEM FOR ASSESSMENT OF COGNITIVE FUNCTION BASED ON ELECTRONIC DEVICE USAGE

CROSS-REFERENCE TO RELATED APPLICATIONS

This application is a continuation-in-part of pending U.S. patent application Ser. No. 14/059,682 filed Oct. 22, 2013 entitled METHOD AND SYSTEM FOR ASSESSMENT OF COGNITIVE FUNCTION BASED ON MOBILE DEVICE USAGE, which is hereby incorporated by reference in its entirety.

BACKGROUND

1. Field of Art

The invention relates generally to computing a person's cognitive function and, more specifically, to unobtrusive assessment of cognitive function from electronic device usage.

2. Background Art

Cognitive function tests measure a person's cognitive abilities across a broad range of cognitive domains such as memory (working memory, semantic memory, episodic memory), attention, processing speed (visuospatial, symbol substitution), verbal skills, general intelligence, and executive function. Today, cognitive function tests are administered by a trained psychometrician requiring several hours of testing and cannot be repeated more frequently than once per year. The test scores can vary due to a change in the person's cognitive function, due to the subjective nature of the interpretation of the tests, or due to situational factors that may affect an individual on the day of the test.

Brain health is critical to our success as individuals in an increasingly cognitive demanding society. In school aged children and adolescents, brain health is responsible for academic success. In working individuals, brain health leads to improved job performance, and in the elderly it enables autonomy, independence and greater enjoyment from activities.

Cognitive function is a measure of brain health, and factors that affect the brain also affect cognitive function. These factors can be categorized into situational, traumatic, and disease related. Situational factors include lifestyle decisions on diet, social engagement, intellectual stimulation, physical activity, sleep patterns, and stress levels. For example, during periods of high stress, poor sleep, and inadequate physical activity, a person will perform worse on a cognitively demanding task [1]. Unfortunately, there is no known reliable system or method for repeated and regular assessment of cognitive function to inform a person of the harm or benefit that current lifestyle decisions have on their brain health. Repeat cognitive function testing by a psychometrician is neither practical nor reliable when repeated more frequently than once per year because the individual acquires test-taking skills for the test. Similarly, the emergence of online tests available through many application vendors such as BrainBaseline [2] suffer test practice effects that are well documented [3,4] whereby the subject develops test taking skills that increase their scores but do not transfer well to real world activities and undermine the test's sensitivity and specificity to cognitive changes.

Traumatic factors affecting cognitive function include blunt or penetrating head injuries. Unlike situational factors, the effect of traumatic brain injury on cognitive function is not generally reversible. Traumatic brain injury is increasingly recognized as a contributor to cognitive function deficits in players of contact sports. Early detection of changes in cognitive function for contact sport athletes is paramount to their brain health and requires a systemic method to measure cognitive function that is repeatable, reliable, and unobtrusive.

Many diseases are known to affect brain health and cognitive function. The progression of aging into mild cognitive impairment and Alzheimer's disease is of great societal concern because of its rapidly increasing prevalence in an increasingly older society. Today, one in eight older Americans has Alzheimer's disease and Alzheimer's is the sixth leading cause of death in the United States [5]. By 2025, the number of Americans age 65 and older with Alzheimer's disease is estimated to increase 30%, and by 2050 that number is expected to triple, barring any breakthroughs to prevent, slow or arrest the disease [5]. Prior to developing Alzheimer's disease, patients go through a six-year prodromal phase of cognitive decline. The societal burden of mental disease in the elderly is staggering and poised to worsen. A repeatable, reliable, and unobtrusive test of cognitive function is needed to monitor brain health in aging adults to enable early detection and intervention.

Mood disorders include depressive disorders, bipolar disorders, and substance-induced mood disorders. They affect people of all ages and impair multiple cognitive domains [6]. In the United States, mood disorders are among the most common reason for hospitalization in children under 18 [7]. With a 12-month adult prevalence of 9.5% [8], mood disorders are a costly social burden. Mood disorder therapy focuses on the behavioral and mood related facets of the disease to the detriment of the cognitive function deficits. Medications to treat mood disorders can worsen cognitive domains such as memory. The impact of cognitive deficits in a person's school or job performance can be significant, is exacerbated by treatment, and frequently unrecognized due to lack of adequate repeatable, reliable, and unobtrusive measures of cognitive function.

Many other diseases are known to affect brain health and cognitive function. These include neurovascular disorders including multi-infract dementia, hepatic failure with encephalopathy, renal failure, congestive heart failure, and various infectious disease and viral illness to name a few. Individuals with any of these disorders are at risk for cognitive impairment and would benefit from repeatable, reliable, and unobtrusive measures of cognitive function.

The introduction of mobile devices and their broad adoption has revolutionized how society interacts both with each other and with their surroundings. A smartphone today enables a user to make calls, send and receive emails and text messages, find their location on a map or retrieve directions to a destination point, browse the internet, download and play game applications, and a host of other activities. In addition, these smartphones are equipped with accelerometers and gyroscopes that sense the device's acceleration and orientation in 3-dimensions. Processing of the acceleration and orientation signals reveals the user's activity such as whether the person is walking or jogging. Mobile devices encompassing wearable electronic devices such as watches, clothing, and glasses [9,10] are also capable of delivering much of the functionality found in a smartphone.

One company that has leveraged the close interaction of an individual with their mobile device to make behavioral assessments is Ginger.io [11,12]. Ginger.io provides a smartphone application that tracks the number and frequency of calls, text messages, and emails sent, and uses the device's global positioning system (GPS) and accelerometer to infer activity level. The target population for Ginger.io's application is patients with chronic diseases such as diabetes, mental disorders, and Crohn's disease. When a patient deviates from their routine behavior of calling and texting patterns, Ginger.io alerts the individual's caregiver to intervene and assess the situation for noncompliance with medications, inappropriate titration of medications, and other factors that may precipitate a flare-up of the patient's disease. This approach is behaviorally based and does not measure cognitive function but rather changes in behavior that may be attributed to a preexisting disorder flare up.

Recent research supports a close interaction between motion and cognition, largely mediated by interconnections between the cerebellum responsible for motion and areas in the brain such as the prefrontal cortex responsible cognition [13,14]. Sensors in an electronic device, including wearable devices, provide insights into the user's motion and enable detection of irregularities or changes in motion.

What is needed is a method and system to assess cognitive function that is repeatable, reliable, and unobtrusive to an individual.

1. Lieberman H R, Tharion W J, Shukitt-Hale B, Speckman K L, Tulley R, Effects of caffeine, sleep loss, and stress on cognitive performance and mood during U.S. Navy SEAL training. *Psychopharmacology*, 2002, 164:250-261
2. www.brainbaseline.com
3. Ackerman P L, Individual differences in skill learning: An integration of psychometric and information processing perspectives. *Psychol Bull*, 1987, 102:3-27
4. Healy A F, Wohldmann E L, Sutton E M, Bourne L E, Jr, Specificity effects in training and transfer of speeded responses. *J Exp Psychol Learn Mem Cognit*, 2006, 32:534-546
5. Alzheimer's Association, 2012 Alzheimer's Disease Facts and Figures. www.alz.org/downloads/facts_figures_2012.pdf
6. Marvel, Cherie L., and Sergio Paradiso. "Cognitive and neurological impairment in mood disorders." *The Psychiatric clinics of North America* 27.1 (2004): 19.
7. Pfuntner A., Wier L. M., Stocks C. Most Frequent Conditions in U.S. Hospitals, 2011. HCUP Statistical Brief #162. September 2013. Agency for Healthcare Research and Quality, Rockville, Md.
8. Kessler R C, Chiu W T, Demler O, Walters EE. Prevalence, severity, and comorbidity of twelve-month DSM-IV disorders in the National Comorbidity Survey Replication (NCS-R). Archives of General Psychiatry, 2005 June; 62(6):617-27.
9. http://www.crunchwear.com
10. http://en.wikipedia.org/wiki/Google_Glass
11. www.ginger.io
12. Owen Covington, 'Virtual nurse' helps Forsyth Medical Center track diabetics. *The Business Journal*, May 2013, http://www.biziournals.com/triad/news/2013/05/20/forsyth-medical-center-using-virtual.html
13. Koziol L F, Budding D, Andreasen N, D'Arrigo S, Bulgheroni S, et al. (2013) Consensus Paper: The Cerebellum's Role in Movement and Cognition. Cerebellum: Cerebellum (2014) 13:151-177
14. Jensen E. *Teaching with the Brain in Mind*, $2^{nd}$ Edition. Association for Supervision & Curriculum Deve; Revised 2nd edition, 2005

BRIEF SUMMARY OF INVENTION

The invention enables a person to monitor changes in their or another's cognitive function in an unobtrusive manner, to view those changes over time, and to evaluate the impact on that changes in social engagement, physical activity, learning activity, and diet have on their cognitive function evaluation. What is needed is a method and system to assess cognitive function that is highly sensitive, specific, and unobtrusive to an individual. Such a method and system would measure and track a person's cognitive function without explicit input or behavioral changes required by the subject, such as repeated neuropsychological evaluations and online tests. Rather, the method and system would use digitally recorded interactions of an individual with their electronic devices, such as mobile devices and wearable electronics, to compute measures of cognitive function, detect changes in cognitive function, and infer attribution to changes in behavioral activity without disrupting the user's day-to-day activities or their use of electronic devices.

One embodiment of the present invention is a method for unobtrusively recording an individual's interaction with an electronic device that may include applications opened, inputs typed, gesture patterns used on a touch-screen, body motions, eye-movements and voice input. The method of the present invention may include the step of recording data from the electronic device's global positioning system (GPS), accelerometer, and gyroscope to infer daily activity including the activity intensity, daily mobility including method of travel, and daily social engagement through latitude and longitude localization of travel destination to a shopping center, a museum, or a restaurant. This data may provide insight regarding an individual lifestyle, including their social skills, level of activity and dietary habits. These insights may contribute to good health and/or they may be indicative of a problem. The method of the present invention may further include the step of recording data from the electronic device's phone, email, and texting applications to capture incoming and outgoing calls, emails and texts generated, length of conversation, length of messages, and discrepancies in voice messages and email messages opened versus received, which are used as additional inputs to infer changes in social engagement.

The method of the present invention can further include the step of recording data from a barcode scanning application used to scan purchased grocery items, food and beverages consumed, and supplementing that data with nutritional fact information to track diet attributes such as caloric input, calories from fat, consumed saturated fats, trans fats, cholesterol, sugars, protein, vitamins and minerals. The method of the present invention may also include the step of recording medications taken, dosages, and quantities. This information is also indicative of lifestyle that is healthy or not. This information can also correlate to an increase or decline in an individual's cognitive function. The method of the present invention can further include the step of recording data from wearable devices that measure, by way of example, heart-rate, blood oxymetry, body temperature, electroencephalogram, and communicate that information to an application resident on a mobile device to infer the user's physical activity, activity intensity, and learning activity. This information related to an individual's biological vitals may explain why there is a change in cognitive function and why the change is not problematic and/or this information can be an indicator of a systemic problem that will have a long term negative impact on cognitive function. The method may further include the step of recording the URLs visited on an internet browser application, e-book pages read on an e-book application resident on the electronic device, the content classification of the material read and its level of complexity, and the language of the content, to further infer learning activity by the user.

The data captured from the user's electronic device by the method of the present invention is preferably persisted in the device's storage and further transmitted to a cloud computing system to compute cognitive function from the user's interactions and to infer behavioral activity attribution effects on changes in cognitive function. The cognitive function assessment and behavioral activity attributions are preferably presented to the user in a password protected online portal that reveals positive and negative contributors to trends in cognitive function assessment and establishes behavioral targets to improve cognitive function. Those targets, and any ensuing improvement or decline in cognitive function may be subsequently measured by the method of the present invention, enabling an unobtrusive, closed-loop method and system for assessing and improving cognitive function from electronic device usage. The cloud computing environment preferably allows a user to change electronic devices and/or electronic device service carriers and still have access to previously recorded data.

These and other advantageous features of the present invention will be in part apparent and in part pointed out herein below.

BRIEF DESCRIPTION OF THE DRAWING

For a better understanding of the present invention, reference may be made to the accompanying drawings in which.

Figure 1:
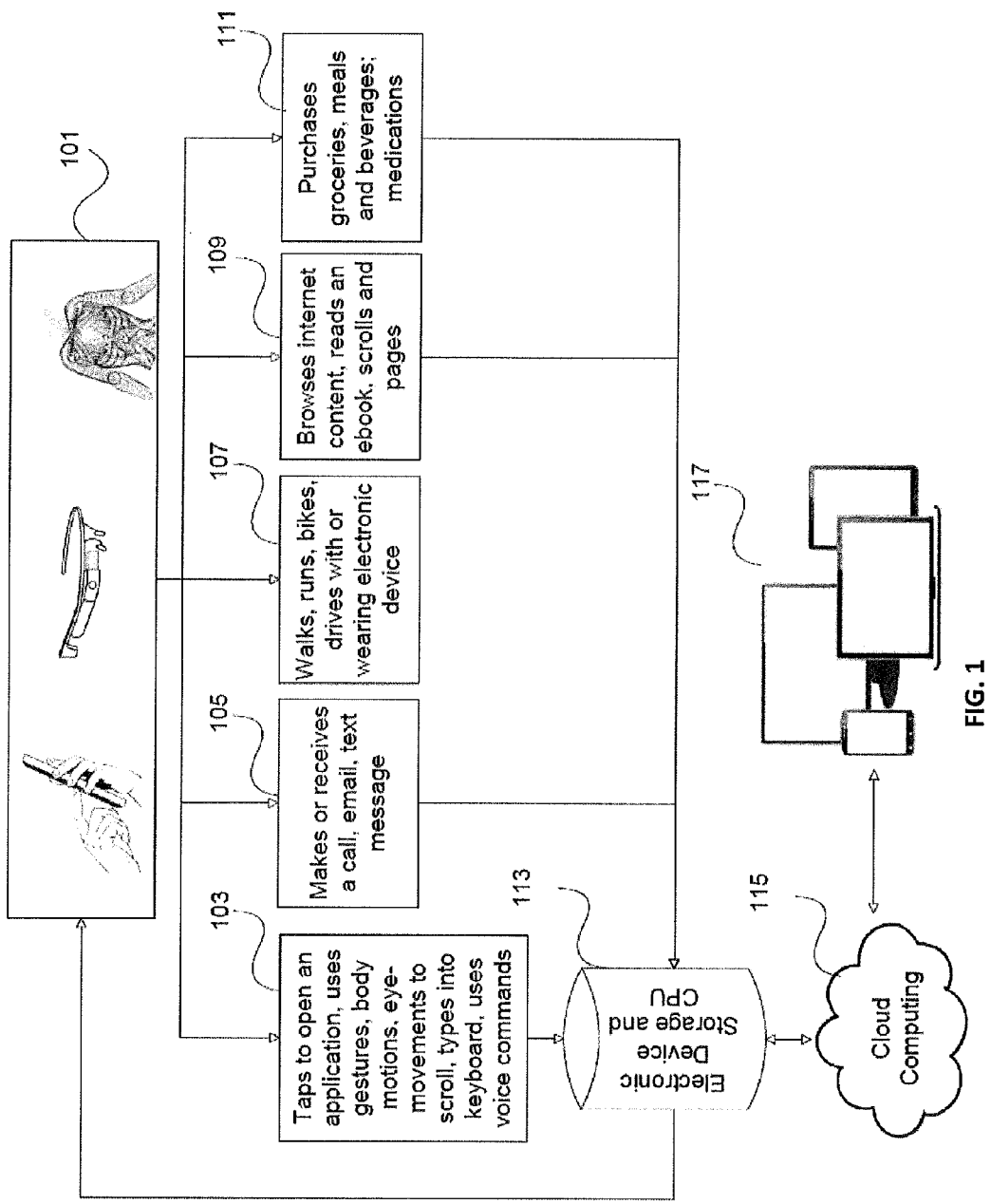
FIG. 1 illustrates an embodiment of the unobtrusive cognitive function assessment system configured in accordance with the present invention.

While the invention is susceptible to various modifications and alternative forms, specific embodiments thereof are shown by way of example in the drawings and will herein be described in detail. It should be understood, however, that the drawings and detailed description presented herein are not intended to limit the invention to the particular embodiment disclosed, but on the contrary, the intention is to cover all modifications, equivalents, and alternatives falling within the spirit and scope of the present invention as defined by the appended claims.

DETAILED DESCRIPTION

According to the embodiment(s) of the present invention, various views are illustrated in FIG. 1-8 and like reference numerals are being used consistently throughout to refer to like and corresponding parts of the invention for all of the various views and figures of the drawings.

The following detailed description of the invention contains many specifics for the purpose of illustration. Any one of ordinary skill in the art will appreciate that many variations and alterations to the following details are within scope of the invention. Accordingly, the following implementations of the invention are set forth without any loss of generality to, and without imposing limitations upon, the claimed invention.

One implementation of the present invention comprises a system and method that enables an unobtrusive assessment of a person's cognitive function from electronic device usage, and in which an embodiment preferably teaches a novel system and method for recording on the electronic device the occurrence and timing of user events comprising the opening and closing of applications resident on the device, the characters inputted and the touch-screen gestures, tapping, body motions, and eye movements used on those applications, further recording the kinetic activities of motion, gait and balance from wearable gyroscopic and accelerometer sensors. The embodiment further preferably includes performing the step of learning a function mapping from the electronic device recordings to measurements of cognitive function for a population of users that uses a loss function to determine relevant features in the recording, identifies a set of optimal weights that produce a minimum of the loss function, creates a function mapping using the optimal weights. Further, the embodiment may include performing the step of applying the learned function mapping to a new recording from the electronic device of new users or from the same population of users to compute a new cognitive function value. For the cognitive function, a linear or nonlinear functional model can be used that inputs the recorded activity by the electronic device, and subsequently outputs a cognitive function measurement. In one embodiment, the cognitive function model is estimated, or fit, to the data recorded from electronic devices for a population of users for which baseline cognitive function measurements are available. The cognitive function model is then applied to new recordings from the electronic devices of new users or from the same population of users to compute a new cognitive function value. In another embodiment, the cognitive function of a user is the percentile rank of a metric computed from the data recorded from the user's electronic device when compared to all users. Diet, medications, stress, chronic lack of sleep, disease, and mood disorders such as depression can all temporally affect cognitive function and would be reflected in repeated evaluations of the cognitive function model upon receiving input data from a user's electronic device. Powerful nonlinear models include neural networks and deep belief networks, a machine learning function composed of layers of neural networks capable of learning complex high-level features. A software application can reside on an electronic computing device, such as a smart phone, personal data assistant (PDA), tablet computer, or wearable electronics such as glasses, watches, or clothing such that when it is executed by the processor of the computing device, the steps of the method may be performed.

Another implementation of the present invention comprises a system and method that enables a person to unobtrusively quantify the effect of physical activity on cognitive function, in which the embodiment teaches a novel system and method for repeatedly recording on the electronic device one of global positioning system longitude and latitude coordinates, accelerometer coordinates, and gyroscope coordinates. The implementation further performs the step of learning a function mapping from those recordings to measurements of cognitive function using a loss function to identify a set of optimal weights that produce a minimum for the loss function, uses those optimal weights to create the function mapping, and the embodiment further includes performing the step of computing the variance of the cognitive function measurements that is explained by the function mapping to assign an attribution to the effect of physical activity on measured changes in cognitive function. For example, a mixed model function is a type of function containing both fixed and random effects and is used in settings where repeated measurements are made over time on the same subjects. The mixed model function can be utilized for the learned function mapping, which develops the appropriate attribution physical activity levels to the cognitive function from the repeated measurements.

A further implementation of the present invention comprises a system and method that enables a person to unobtrusively quantify the effect of social activity on cognitive function, which embodiment teaches a novel system and method for repeatedly recording on the electronic device one of outgoing and incoming phone calls, outgoing and incoming emails, and outgoing and incoming text messages. The implementation further includes performing the step of learning a function mapping from those recordings to measurements of cognitive function using a loss function to identify a set of optimal weights that produce a minimum for the loss function, uses those optimal weights to create the function mapping, and the embodiment further includes performing the step of computing the variance of the cognitive function measurements that is explained by the function mapping to assign an attribution to the effect of social activity on measured changes in cognitive function.

A further implementation of the present invention comprises a system and method that enables a person to unobtrusively quantify the effect of learning activity on cognitive function, which embodiment teaches a novel system and method for repeatedly recording on the electronic device one of URLs visited on an internet browser application, books read on an e-reader application, and/or games played on game applications. The implementation further may include performing the step of learning a function mapping from those recordings to measurements of cognitive function using a loss function to identify a set of optimal weights that produce a minimum for the loss function and uses those optimal weights to create the function mapping. The embodiment further includes performing the step of computing the variance of the cognitive function measurements that is explained by the function mapping to assign an attribution to the effect of learning activity on measured changes in cognitive function.

A further implementation of the present invention comprises a system and method that enables a person to unobtrusively quantify the effect of diet and medications on cognitive function, which the embodiment teaches a novel system and method for repeatedly recording on the electronic device the nutritional content of food consumed, caloric intake by food group, alcohol, caffeine and medications taken, dosages, and frequency thereof. The implementation further includes performing the step of learning a function mapping from those recordings to measurements of cognitive function using a loss function to identify a set of optimal weights that produce a minimum for the loss function and uses those optimal weights to create the function mapping. The embodiment further includes performing the step of computing the variance of the cognitive function measurements that is explained by the function mapping to assign an attribution to the effect of diet and medications on measured changes in cognitive function.

The loss function for the cognitive function can evaluate baseline recordings and changes and trends in the recordings both from a quantitative and qualitative perspective. For example the frequency of events can be monitored for cognitive measurement as well as the quality of each event, such as latencies between gestures, tapping, body motions, eye movements or keystrokes, erroneous keystrokes or gestures, duration of key presses, misspellings and kinetic activities of motion, gait, or balance that are captured by wearable electronic sensors and recorded or transmitted to an electronic device.

Another implementation of the invention can be a computer system comprising a mobile computer (for example a smart-phone; tablet or PDA computing device; wearable electronic accessories such as glasses or watches and wearable electronic clothing) including a wireless network interface which communicates over a wireless network with a second computer including a network interface, each computer further including a processor, a memory unit operable for storing a computer program, an input mechanism operable for inputting data into said computer system, an output mechanism for presenting information to a user, a bus coupling the processor to the memory unit, input mechanism and output mechanism, and wherein the mobile computer system includes various executable program modules stored thereon where when executed are operable to perform functions.

The computer system may comprise a data collection module stored on a mobile computer where, when executed, records to the memory unit of said mobile computer the occurrence and timing of user events comprising the opening and closing of applications resident on said mobile computer, the characters inputted in said applications, the touch-screen gestures, tapping, body motions, and eye movements made on said applications. The type of the event and both the frequency and timing of the events and the various qualitative metrics regarding the event are recorded. A transmission module can also be stored on said mobile computer that when executed transmits through the wireless network interface the recordings stored in the memory unit to said second computer. A feature extraction module and metric computation module can be stored on said second computer that when executed learns a function mapping from said transmitted recording to measurements of cognitive function using a loss function to determine relevant features (including frequency, timing and qualitative metrics) in said recording, identifies a set of optimal weights that produce a minimum for said loss function, and creates said function mapping using said optimal weights. After learning the function mapping, the same feature extraction and metric computation modules when executed applies said function mapping to a new transmitted recording of the occurrence and timing of events comprising the opening and closing of applications resident on said device, the characters inputted in said applications, the touch-screen gestures, tapping, body motions, and eye movements used on those applications, the kinetic activities of motion, gait and balance recorded from wearable gyroscopic and accelerometer sensors, to calculate a new cognitive function value.

Another implementation of the invention can be a computer system comprising a mobile computer including a wireless network interface which communicates with a second computer including a network interface, each computer further including a processor, a memory unit operable for storing a computer program, an input mechanism operable for inputting data into said computer system, an output mechanism for presenting information to a user, a bus coupling the processor to the memory unit, input mechanism and output mechanism, wherein the mobile computer system includes various executable program modules stored thereon where when executed are operable to perform functions.

The computer system can comprise a motion module stored on said mobile computer where when executed records to the memory unit of said mobile computer one of global positioning system longitude and latitude coordinates, accelerometer coordinates, and gyroscope coordinates. In another implementation, the computer system can comprise a social module stored on said mobile computer that when executed records to the memory unit of said mobile computer one of outgoing and incoming phone calls, outgoing and incoming emails, and outgoing and incoming text messages. In another implementation, the computer system may comprise a learning module stored on said mobile computer that when executed records to the memory unit of said mobile computer at least one of: URLs visited on an internet browser application, books read on an e-reader application, and games played on game applications. In another implementation, the computer system may comprise a diet and medication module stored on said mobile computer that when executed records nutritional content of food consumed, caloric intake by food group, medications taken, dosages and frequencies thereof.

In any of the preceding implementations, a transmission module can be stored on said mobile computer that when executed transmits through the wireless network interface the recordings stored in the memory unit to said second computer. In any of the preceding implementations, an attribution module can be stored on said second computer that when executed learns a function mapping from said transmitted recording to measurements of cognitive function using a loss function to identify a set of optimal weights that produce a minimum for said loss function, and creates said function mapping using said optimal weights. In any of the preceding implementations, a reporting module can be stored on said second computer where when executed presents to the user the computed cognitive function metrics and the attribution to said metrics that are explained by said recordings.

The details of the invention and various embodiments can be better understood by referring to the figures of the drawing. FIG. 1 illustrates an embodiment of the functional description of the system configured in accordance with the present invention and is not intended to limit scope as one of ordinary skill would understand on review of this application that other configurations could be utilized without departing from the scope of the claimed invention. Referring to FIG. 1 an individual uses his or her electronic device 101 which may be a smart phone or tablet computer; a wearable electronic device such as electronic glasses, electronic wristband device, or smart clothing; or a household electronic device such as a desktop computer or a remote control. In 103, the individual taps a touch-screen, speaks, uses a touch pad, or invokes an external device such as mouse to open an application; uses touch-screen gestures, eye movements, body motions including head tilting and swiping, or invokes an external device such as mouse to scroll within an application; types messages, directions, and other content on a keyboard exposed by the application or uses voice commands to do the same; reads and scrolls through content, and makes calls or listens to messages. The user's activity in 103 is recorded on the device's persistent storage 113. The storage 113 being of the type generally some known in the art. In 105, the user makes or receives phone calls, email messages, and text messages in a manner known in the art.

The date and time of a user's activity, the activity duration, and the sender and recipient phone number or email address are preferably recorded in the device's persistent storage 113. The frequency of each event may be recorded and the various qualitative characteristics of each event may also be recorded. In 107, when the electronic device is also a mobile or wearable device, the user preferably carries the electronic device with them while driving, using public transportation, walking, biking or running or when the user is otherwise in motion. While engaging in these activities, the device's global positioning system (GPS) records the user's longitude and latitude coordinates in 107. Similarly, in 107, the device's acceleration and gyroscopic motion along a 3-coordinate system is preferably recorded. The type of locations to which the individual traveled may be determined and the characteristic of the motion of the user may also be evaluated for fluidity or erratic motion. This information is also preferably recorded in the device's persistent storage 113. In 109, the user may browse URLs on an internet-browser application resident on the electronic device and/or reads an e-book on an e-book reader resident on the device. The URLs browsed and/or the pages of the e-book read, the start time and end time between URLs and pages may be recorded by 109 and persisted in 113.

Note that all gesture activity, typing activity, and voice command activity during the use of applications tracked in 105, 107, and 109 is preferably captured separately in 103 and recorded with the time and application in which that activity took place. In this way, the system tracks gestures used during browsing, paging and scrolling, for example. Lastly, in 111 a bar code scanning application and medical reminder application that may be resident on the electronic device preferably enables the user to scan grocery purchases and/or meals and beverages purchased when the latter have bar codes. The bar code scanning application preferably has access to a database of nutritional facts. If the nutritional facts for the scanned bar code is not in the database, then in 111 the application may instruct the user to photograph the nutritional fact label of the item. The bar code information and the medications taken, dosages, and frequencies are also preferably persisted in 113.

The data captured in the device's persistent storage 113 may be transmitted to cloud computers 115. Transmission preferably uses a secure channel and can use hypertext transfer protocol secure (HTTPS) to securely transfer the data to 115. The cloud computers 115 may analyze the recorded data against historical recordings and against recordings of other users including users that are demographically matched to the existing user. The outputs of the analyses are preferably one or more cognitive function measures. Further outputs may include the effect that behavioral activities, inferred from the activities recorded in 105-111, had on the various cognitive function measures. These behavioral activities include social engagement 105, physical activity 107, learning activity 109, and/or diet and medications 111. The user or the user's delegate in 117 may log into a password protected online account to view these outputs.

In another embodiment of the invention the outputs of the analyses by the cloud computers 115 are transmitted back to the device's persistent storage 113. The user views the outputs directly in the display screen of the electronic device 101.

In yet another embodiment of the invention, the metric computation modules of FIG. 7(b) or FIG. 7(c) and described herein below are resident on the electronic device 113. In this embodiment, the cognitive function metrics are computed locally on the device and the user views the outputs directly in the display screen of the electronic device 101. The outputs may also be transmitted to the cloud computer 115, and the user or the user's delegate in 117 may log into a password protected online account to view these outputs.

In one implementation of the method and system, in order to establish a baseline of data, supervised benchmark testing can be conducted on an initial test group of individuals where these individuals take a neuropsychological benchmark test for cognitive function, and the data is stored. Each of the same individuals who are tested can be provided with mobile devices having the computer program for performing the system and method described herein. Data for each individual can be recorded as outlined herein, and the data from the mobile device usage can be correlated to the benchmark testing results and cognitive function. Cognitive function levels and bands may also be determined from the result. Once certain baselines have been established and correlations are made between cognitive function and mobile device usage, all subsequent mobile device usage by individuals may be utilized to improve the system and method as learning occurs. The learning from the subsequent mobile device usage may be considered unsupervised learning.

Figure 2:
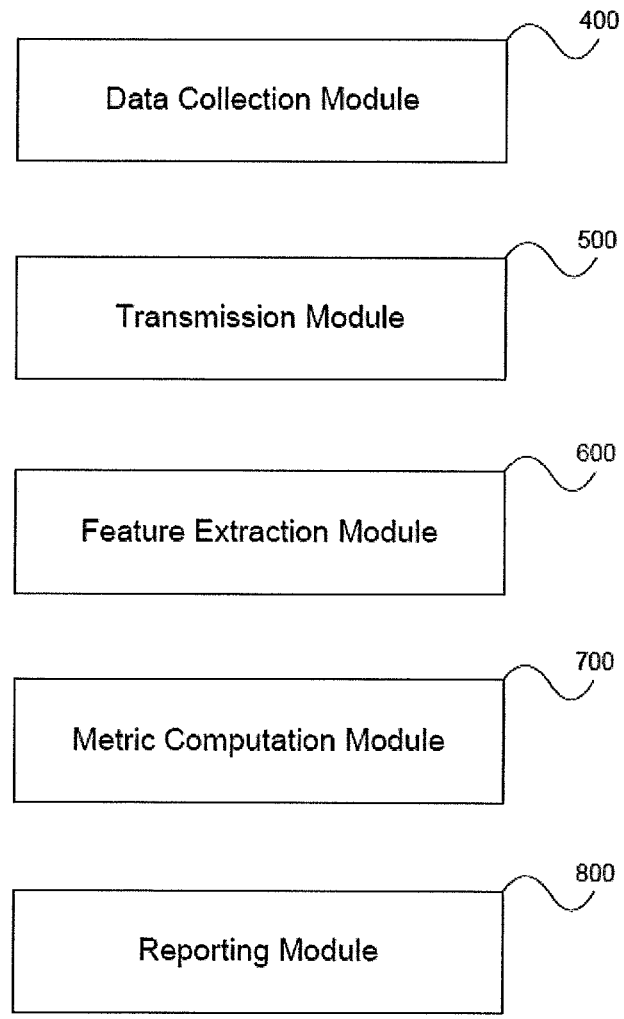
FIG. 2 is a functional description of the unobtrusive cognitive function assessment system in accordance with one embodiment of the present invention.

FIG. 2 illustrates an embodiment of the functional description of the system configured in accordance with the present invention and is not intended to limit scope, as one of ordinary skill would understand on review of this application that other configurations could be utilized without departing from the scope of the claimed invention. Referring to FIG. 2, a user's interaction with an electronic device may be captured and recorded by the data collection module 400 resident on the device. The transmission module 500 is preferably resident on the device and responsible for transmitting and receiving data to and from the cloud computers. This module preferably uses broadband WIFI for the transmission when available, but may alternatively use other transmission means including 4G LTE transmission provided by subscriber data plans. Transmission module 500 preferably is also responsible for securing an encrypted channel.

The feature extraction module 600 may extract patterns and features from the data acquired by one or more of the user's electronic devices using the data collection module 400 resident on each device. In one embodiment of the present invention, feature module extraction 600 is resident on cloud computers. In another embodiment of the present invention, feature extraction module 600 is resident on the device itself, and features are extracted from data acquired by data collection module 400 on that device. The metric computation module 700 may maintain predictive models of cognitive function measures that it takes as input features from feature extraction module 600. In one embodiment of the present invention, the predictive models of metric module computation 700 are resident on cloud computers. In another embodiment of the present invention, the predictive models of metric module computation 700 and the feature extraction module 600 are both resident on the device itself and take as input features extracted from data collected on that device. The metric computation model 700 may also be responsible for learning the predictive models of cognitive function measures from a population of users for which both feature data and traditional cognitive function testing data is available.

Metric module computation 700 may also compute the attribution to the user's cognitive function measures of the user's behavioral activities inferred from data acquired by data collection module 400. A reporting module 800 preferably provides an online login account for the user or the user's delegate to review trends in the user's cognitive function measures, attribution of recent behavior activity to those trends, how well the user is tracking to target behavior activity and target cognitive function, and further may enable the user to update those targets.

Figure 3:
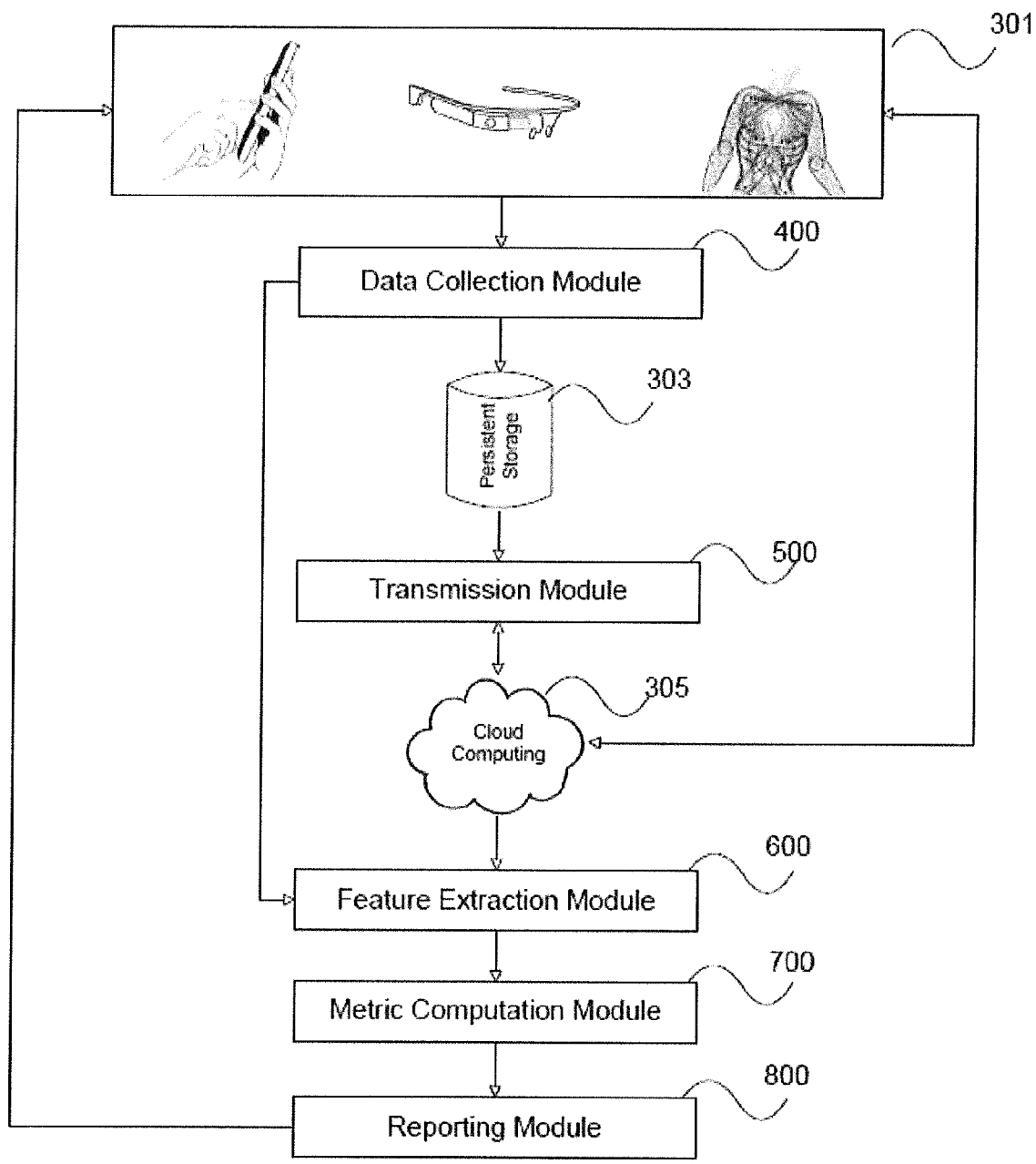
FIG. 3 illustrates an exemplary computing environment of the unobtrusive cognitive function assessment system configured in accordance with one embodiment of the present invention.

FIG. 3 illustrates an embodiment of the computing environment of the system configured in accordance with the present invention and is not intended to limit scope as one of ordinary skill would understand on review of this application that other configurations could be utilized without departing from the scope of the claimed invention. Referring to FIG. 3, a user may download and install a software application to their electronic device 301 from a computer associated with the cloud 305. In one embodiment of the present invention, the software application comprises the data collection module 400 and the transmission module 500. These two modules 400, 500 preferably read and write to the electronic device's persistent storage 303. The data collection module 400 may write raw activity data to the persistent storage 303. The transmission module 500 may transmit the data persisted in storage 303 to the cloud computers 305. The feature extraction module 600, metric computation module 700, and reporting module 800 are preferably resident in the cloud computers 305. Feature extraction module 600 may extract patterns and features from the data that are used as inputs to the metric computation module 700. The metric computation module 700 may output the cognitive function measures. Metric computation module 700 may also output the attribution of the user's behavioral features to the cognitive function measures. The reporting module 800 may create summary reports presented to the user or the user's delegate in a password-protected account on the cloud servers.

In another embodiment of the present invention, the software application comprises the data collection module 400, the transmission module 500, the feature extraction module 600, and the metric computation module 700, and the reporting module 800. Modules 400, 500, 600, 700, 800 are preferably resident on the electronic device. The data collection module 400 may write raw activity data to the persistent storage 303. Feature extraction module 600 may extract patterns and features from the data locally on the device, and metric computation module 700 may use those features to compute cognitive function metrics. Metric computation module 700 may also output the attribution of the user's behavioral features to computed cognitive function metrics. The reporting module 800 preferably displays to the user the outputs of metric computation module 700. Transmission module 500 may communicate with cloud servers 305 and can optionally transmit the outputs of metric computation module 700 to a cloud-based reporting module accessible to the user and the user's delegates. Transmission module 500 may also download updates to the software application.

Figure 4:
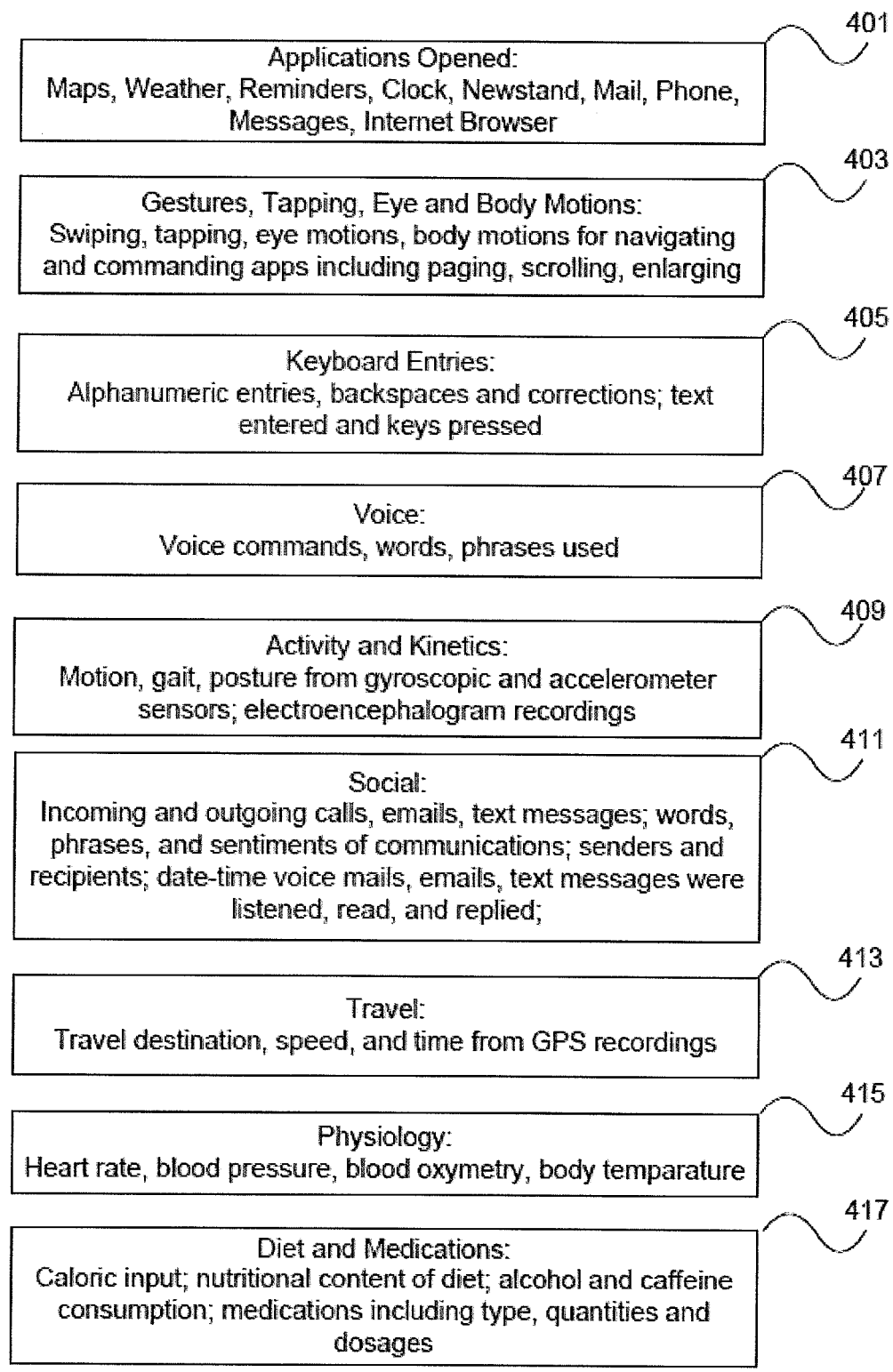
FIG. 4 is a data collection module in accordance with one embodiment of the present invention.

Referring to FIG. 4, an electronic device such as smartphone, a tablet computer, desktop computer, wearable electronic clothing or accessories and other similar devices may have many applications available to the user. These applications include, but are not limited to, maps used for directions and global positioning localization, weather, reminders, clock, newsstand configured with user selected publications, mail configured by the user to include personal and work email, phone configured by the user to include contacts, messages for texting, and an internet browser.

Module 401 preferably tracks the application opened, the date-time that it was opened, date-time that it was closed and records that information on the device's persistent storage. Upon opening an application, a user may interact with the application through one or more keyboard inputs, mouse inputs, voice, gestures, body motions, and eye movements. In 403, applications running on devices that support touch-screen gestures such as tapping and swiping may be recorded. For applications running on wearable electronic devices, 403 records body motion such as head tilting, swiping, or eye movements. Module 403 may record the date-time of the gesture, body motion or eye movement, the duration and latency, the application in use, and the application view change that results from the gesture, body motion, or eye movement. In 405, keyboard entries may be recorded for applications supporting a keyboard entry mode. In 405, all keyboard entries are preferably recorded, which includes for example alphanumeric entries, backspace entries, capitalization, formatting entries, and editing entries. Module 405 further may record the latency and duration of each keyboard entry, the application in use, and the application view change resulting from the key entry. All recordings are preferably stored in the device's persistent storage.

Module 407 may record words and phrases during phone conversations and voice-input commands. Module 407 further may record the application in use, and the application view change resulting from a voice command. All recordings are preferably stored in the device's persistent storage. Module 409 may record sensor data including gyroscope and accelerometer readings from the electronic device, including wearable devices. This data preferably provides information on user activity and kinetic information including motion, gait, and posture when recorded from wearable sensors. Recordings from a wearable electroencephalogram device are also preferably capture by 409. All recordings are preferably stored in the device's persistent storage.

Module 411 may record incoming and outgoing email, text messages, and calls and further may record recipient and sender email addresses, recipient and sender text message phone numbers, and outgoing and incoming phone numbers. This module may further record words, phrases, and sentiment of the communication exchanges. The information is preferably stored in the device's persistent storage together with the date-time of the event.

For electronic devices equipped with a global positioning system (GPS), module 413 may sample the device's location, velocity, altitude, time stamp the input and store it in the device's persistent storage.

Recordings from wearable electronic devices that measure heart rate, blood pressure, pulse oxymetry, body temperature, and other physiological data may be time stamped and recorded in the device's persistent storage in 415. The peripheral accessories can be used to obtain biological vital signs of the individual, which can be used to determine if a decline in cognitive function data is due to a vital sign such as fatigue or low blood-glucose levels rather than an actual decline in cognitive function of the individual. The biological vitals can also be used as an alert of a biological trend that will have a long-term negative impact on cognitive function, such as hypertension.

Module 417 preferably enables a barcode scanning application enhanced with nutritional fact information appended to each barcode entry, that records and timestamps caloric input, nutritional content, alcohol, and caffeine consumption. Medications taken, quantities and dosages may similarly recorded in the device's persistent storage. The dietary information may be used as an alert of a dietary trend that will have a long-term negative impact on cognitive function, such as high alcohol intake or high fat or cholesterol intake. The medication information may be used to determine the negative or beneficial effect that medications and dosages have on cognitive function.

Figure 5:
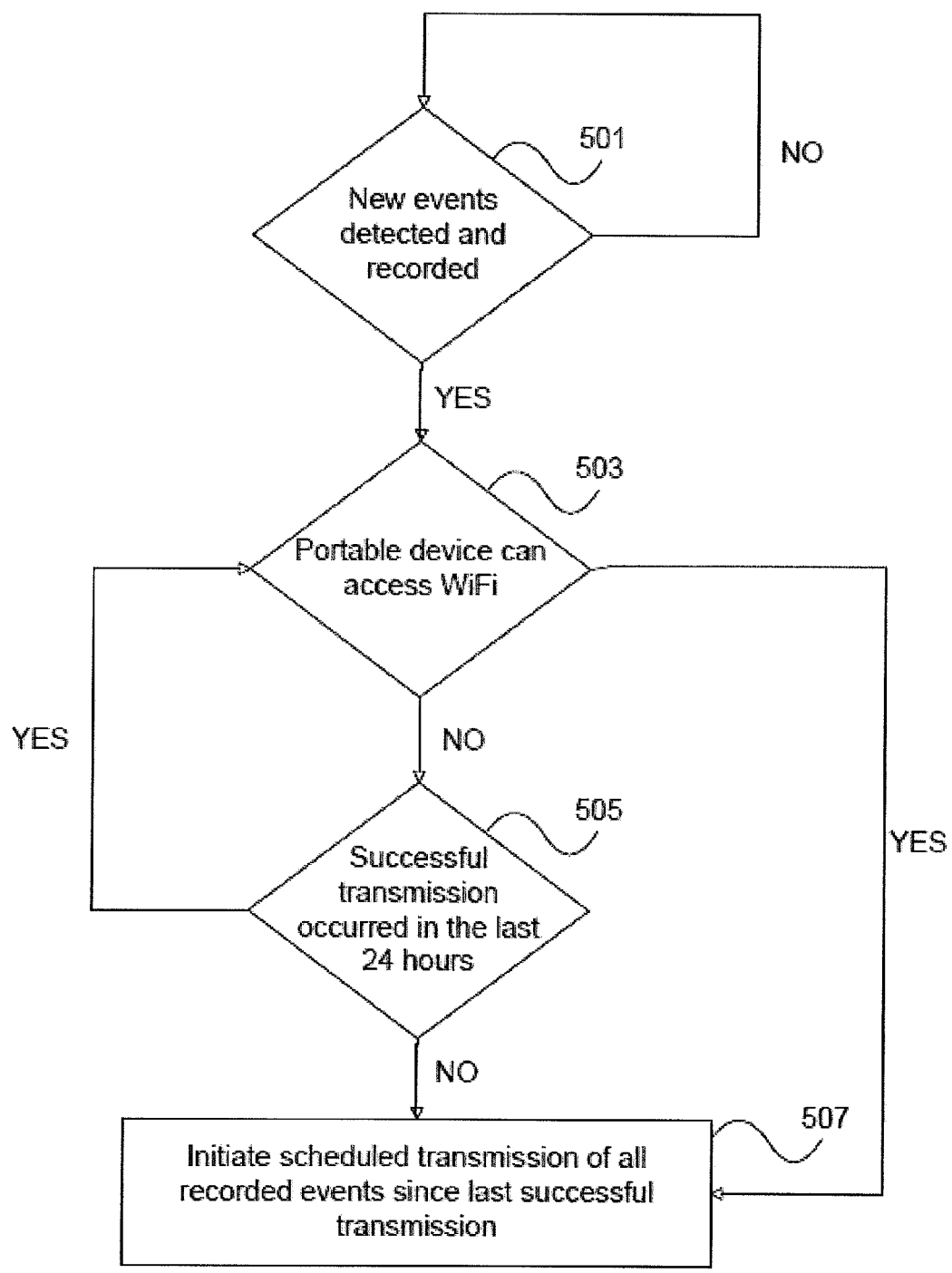
FIG. 5 is a transmission module in accordance with one embodiment of the present invention.

Referring to FIG. 5, the transmission module may be a background process that runs on the electronic device and sleeps until it is awaken by the recording of new events on the device in 501. Upon recording new activity, 501 may pass control to 503 that attempts to establish WIFI access. If 503 succeeds, then it may pass control to 507 to initiate transmission of all recorded activity since the last successful transmission. If 503 fails then it may pass control to 505 of the transmission module which evaluates whether a successful transmission occurred within a 24 hour period. If 505 determines that no successful transmission has occurred within a 24 hour period, it may pass control to 507 to initiate transmission of all recorded activity since the last successful transmission. If, however, 505 confirms that a successful transmission has occurred within 24 hours, it may return control to 503.

Figure 6A:
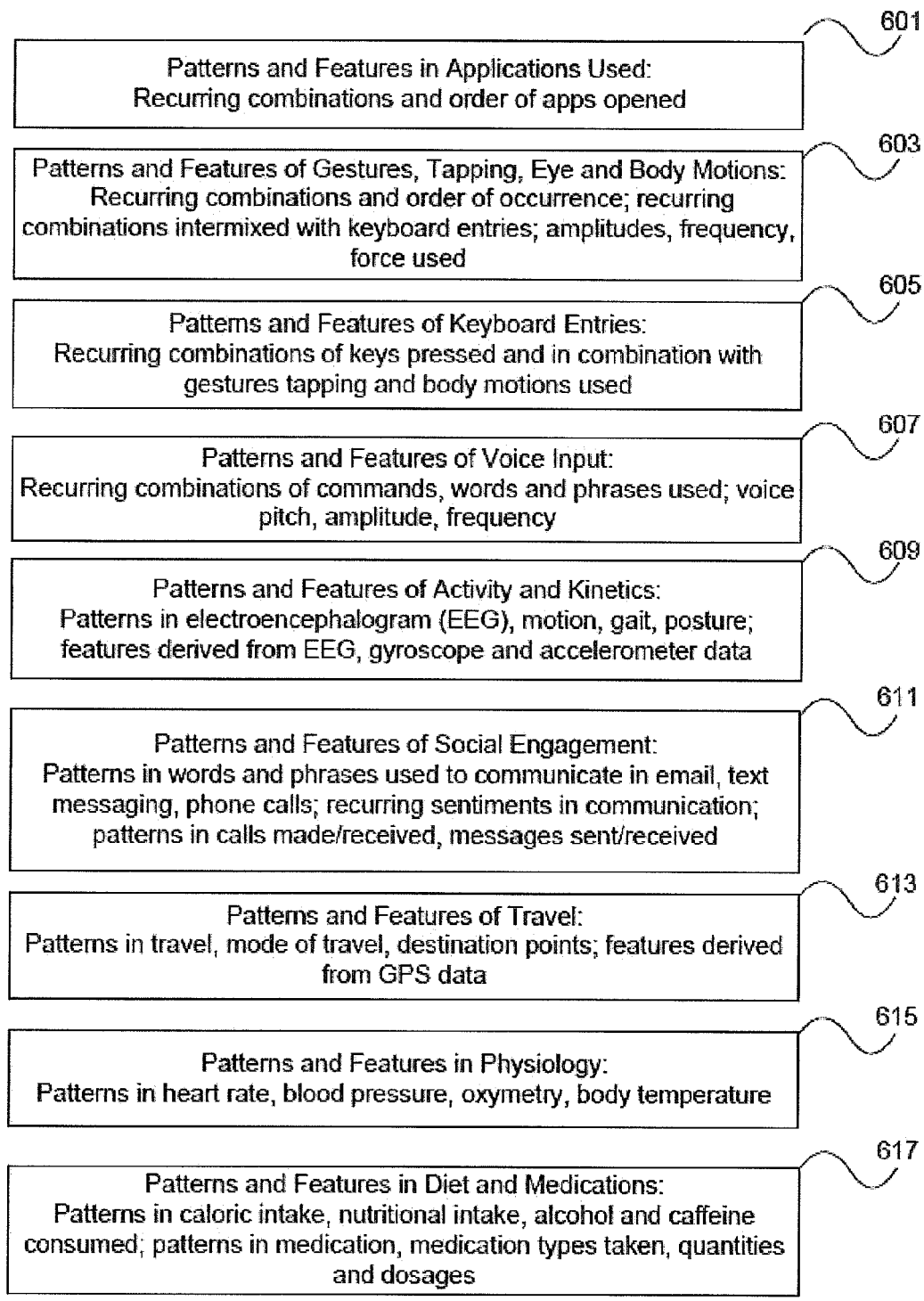
FIG. 6(a)-(b) is a feature extraction module in accordance with one embodiment of the present invention.
Figure 6B:
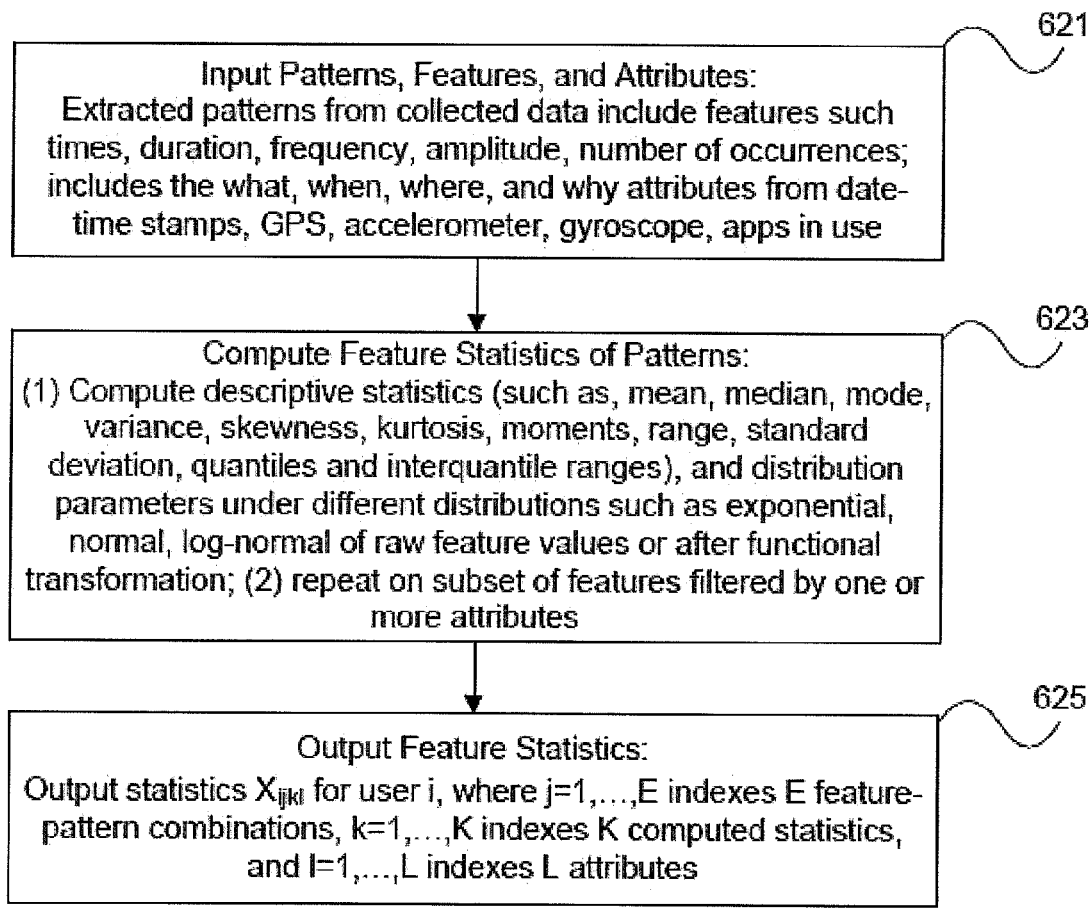

FIGS. 6(*a*) and 6(*b*) illustrate an embodiment of the feature extraction module configured in accordance with the present invention and is not intended to limit scope as one of ordinary skill would understand on review of this application that other configurations could be utilized without departing from the scope of the claimed invention. Referring to FIG. 6(*a*), the cognitive function module may access the recordings made by the data collection module 400. Patterns in a user's interactions with an electronic device are preferably identified and extracted from the data in 601-617. Each pattern has features and attributes that are extracted from the data. The features of each pattern include, for example, timing, duration, frequency and amplitude, and number of occurrences. The attributes of each pattern include information relating to the when, where, what, and why of each pattern. This data includes, for example, date-time of occurrence, GPS readings, accelerometer and gyroscope readings, physiology and kinetic readings, app in use at the time.

In 601, recurring combinations of applications opened and closed by a user, frequency and latencies between opening and closing are preferably identified and extracted. In 603, patterns in a user's gestures, tapping and body motions such as head-tilting, swiping, or eye movements that can be used as commands to an electronic device are preferably identified and extracted from the recorded data. Patterns in false positive rates, scrolling during search and paging during browsing, are also preferably extracted. Features of each pattern including duration, amplitude, frequency, and force used may be extracted when present in the data or derived from the data. In 605, patterns in keys pressed on a keyboard or other input form-factor and in combination with gesture, tapping, body motion and eye movement inputs are preferably identified and extracted. For character inputs, recurring keystroke combinations, recurring spelling mistakes, omissions, back-space corrections, irregular latency variances in common words are preferably extracted. Features of each pattern including duration, frequency, latency, force used, length of messages, and message coherence may be extracted from the data.

In 607, patterns in voice commands, words, and phrases used may be extracted. Following signal processing of the voice, recurring combinations of phones and phoneme may be extracted. Features of each pattern including voice pitch, amplitude, and frequency spectrum are preferably extracted from the data. In 609, patterns in electroencephalogram (EEG), locomotion, gait, and posture recorded from wearable electronic devices are preferably identified and extracted. Features of each pattern derived from the EEG, accelerometer, gyroscope, and other sensor recordings are also preferably extracted.

In 611-617, features and patterns in behavioral activities recorded by module 400 are preferably extracted and used in the metric computation module 700 to explain temporal change in the values of the metrics of cognitive function that are computed from input patterns and features 601-609. In 611, patterns in words and phrases used to communicate in email, text messaging, phone calls, and other communication modes may be extracted. Recurring sentiments in the user's communication and patterns in calls made/received, messages sent/received may also be extracted. Features of each pattern including frequency, duration, and recipient may be extracted with the pattern. The patterns and features of 611 are preferably a proxy to the user's level of social engagement.

In 613, a user's travel, patterns in the inferred mode of travel including vehicle, bicycle, foot or other, patterns in destination points, features of those patterns derived from GPS data and $3^{rd}$ party data such as destination type like restaurant, shopping mall, museum, park, and features like speed of travel, time of day, day of week, date of year are preferably extracted. The patterns and features of 613 may be a proxy to the user's activity and in-person social engagement.

Patterns in heart rate, blood pressure, body temperature, blood oxymetry and other physiologic measurements may be extracted from the data by 615. Together with accelerometer and gyroscope data in 609, a rapid heart rate from anxiety or illness is preferably distinguished from exercise-induced changes. Features of each pattern including maximum and minimum measurements, duration of pattern, frequency of pattern, are also preferably extracted.

In 617, patterns in recorded daily caloric intake, nutritional intake by food group or food type, intake of alcohol, caffeine, medications including prescription and non-prescription may be extracted. Features such as time of day, total intake, and location of intake are preferably derived or extracted from the recorded data.

The what, where, when, and why attributes extracted from the data for each pattern in 601-617 may be used to filter those patterns prior to inputting into the metric computation module 700. They may also be included as covariates in the cognitive function model of 700. For example, including time of day or day of week may explain variance that can be attributed to individual fatigue and other factors that have negative effects on cognitive function. GPS, gyroscope and accelerometer recordings from module 400 may be used to correct for motion artifact from activities such as driving or walking. Lastly, the physiologic measurements of heart-rate, blood pressure, blood oxymetry, body temperature, and electroencephalogram recorded by module 400 may be used to correct for the negative effects that anxiety, general malaise, illness, and fatigue have on cognitive function.

Referring to FIG. 6(*b*), statistics may be computed in 623 from the features and attributes of the patterns 621 that were extracted in 601-617. The statistics may be computed on the raw feature values or after functional transformation of the feature values. The computed statistics may also be computed on all available values of the feature or transformed feature, or they may be computed on a subset of values filtered by one or more attributes. The statistics computed may include, for example, mean, median, mode, variance, kurtosis, moments, range, standard deviation, quantiles, inter-quantile ranges, and distribution parameters under different distributions such as exponential, normal, or lognormal. Each computed statistic for each pattern, feature, and attribute combination is preferably outputted in 625.

Figure 7A:
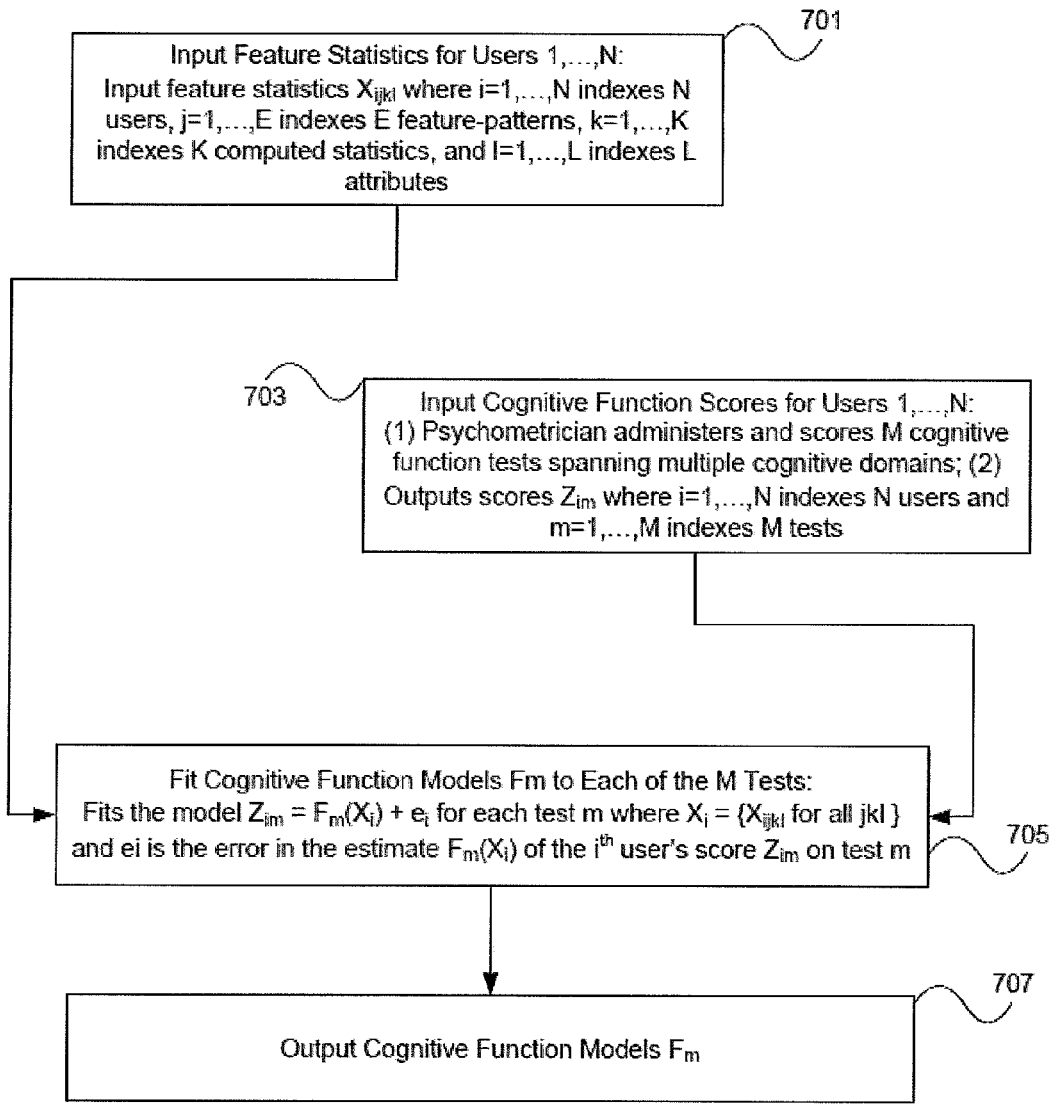
FIG. 7(a)-(c) is a metric computation module in accordance with one embodiment of the present invention.
Figure 7B:
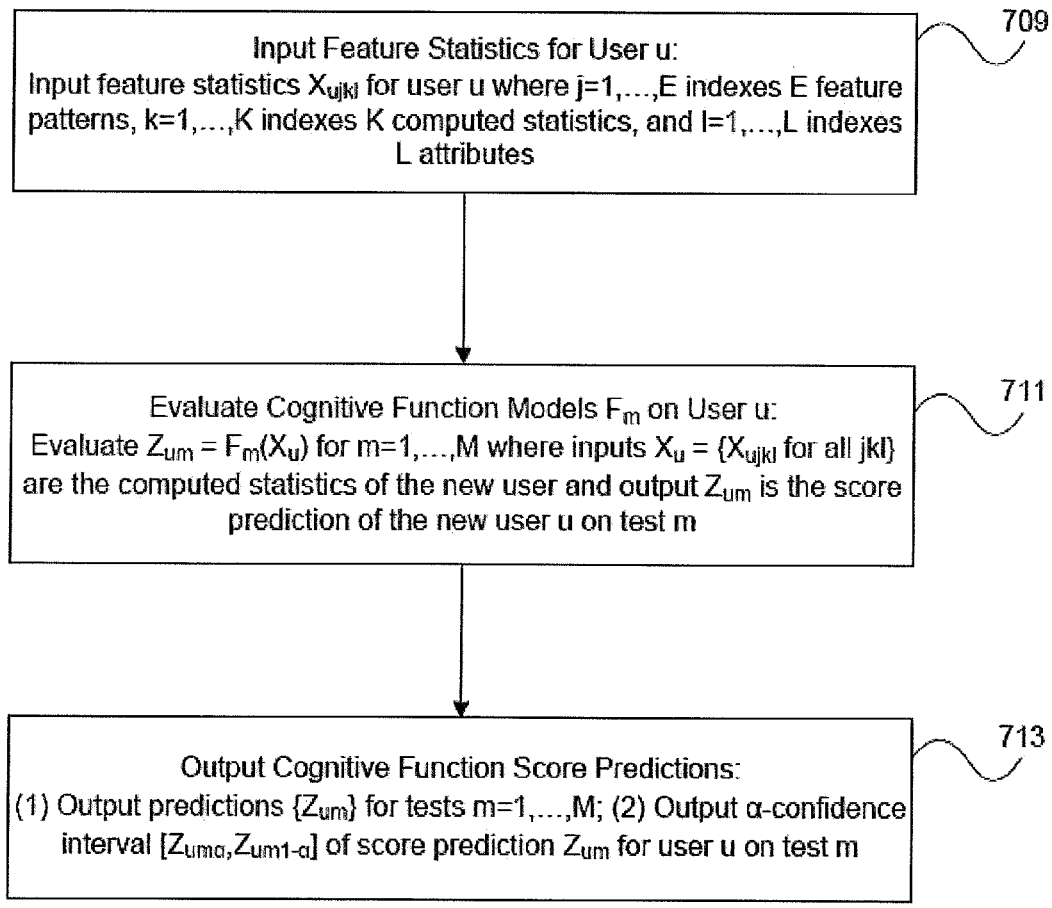

Referring to FIG. 7(*a*), feature statistics 701 indexed by user, pattern, feature, statistic, and attribute for a population of users, and the cognitive function test scores 703 indexed by user and test for the same user population are preferably inputs to 705. The cognitive function tests in 703 may include tests of general intelligence (IQ), memory, attention, executive function and processing speed. These tests may include standardized neuropsychological tests such as the Wechsler Adult Intelligence Scale test, California Verbal Memory Test, Trail-Making (A&B) test, Wechsler Memory Scale-III test, Symbol Digit Modalities test, Wechsler Digit Span test, Conner's Continuous Performance test, Logical Memory test, Brief Visuospatial Memory test, Controlled Oral Word Association (FAS Fluency) test, Animal Naming Test of Verbal Fluency, and the Grooved Pegboard test. The tests may be administered by a psychometrician or taken on a computer. The scores on these tests are numeric and are the inputs shown in 703. In 705, a cognitive function model for each test in 703 is preferably learned using 701 as inputs to the model and the score of the test 703 as the target output of the model. One of several machine learning methods may be used to learn the target test scores 703 from the feature inputs 705. One suitable method includes a feedforward neural network with a single hidden layer of neurons. To train the feedforward neural network, the input feature data and output test score data is split into a training set, a validation set, and a testing set. The training set is used to learn the parameters of the neural network using the well-known backpropagation algorithm jointly with standard gradient descent to minimize the mean-squared error between the target test scores and the predictions made by the feedforward network on the input feature data. Training ends when the mean-squared error of the validation data (not the training data) reaches a minimum to reduce the risk of over-fitting the data. The test data is used to confirm that the trained network generalizes to new data. Further testing can be achieved by cross-validation of the network on the training data. Other machine learning methods may be suitable as any one of ordinary skill in the art will appreciate. The fitted cognitive function model may be outputted in 707 and generalizes to new input feature data and outputs the test score of the neuropsychology test for which it was trained. One of ordinary skill would understand on review of this application that many functional models and fits of the model are plausible to output a predictive model of user test scores 703 from the user feature statistics 701.

Referring to FIG. 7(*b*), the output cognitive function models in 707 of FIG. 7(*a*) are preferably used to output predictions of cognitive function test scores for the M tests on new input feature statistics 709 indexed by user, pattern, feature, statistic, and attribute. The new input feature statistics 709 may be for a new user for which cognitive function test scores are not available, or they may be feature statistics of a user in the same population used to fit the model in 707 but not the same feature statistics used in 707, for example, feature statistics obtained at a later date under different circumstances for that user. The cognitive function models for each test are preferably evaluated in 711 on the new feature statistics and in 713 the score prediction for each cognitive function test is preferably outputted together with α-confidence intervals around each prediction for a between 0 and 1. The α-confidence intervals are calculated in a manner known and recognized in the art.

Figure 7C:
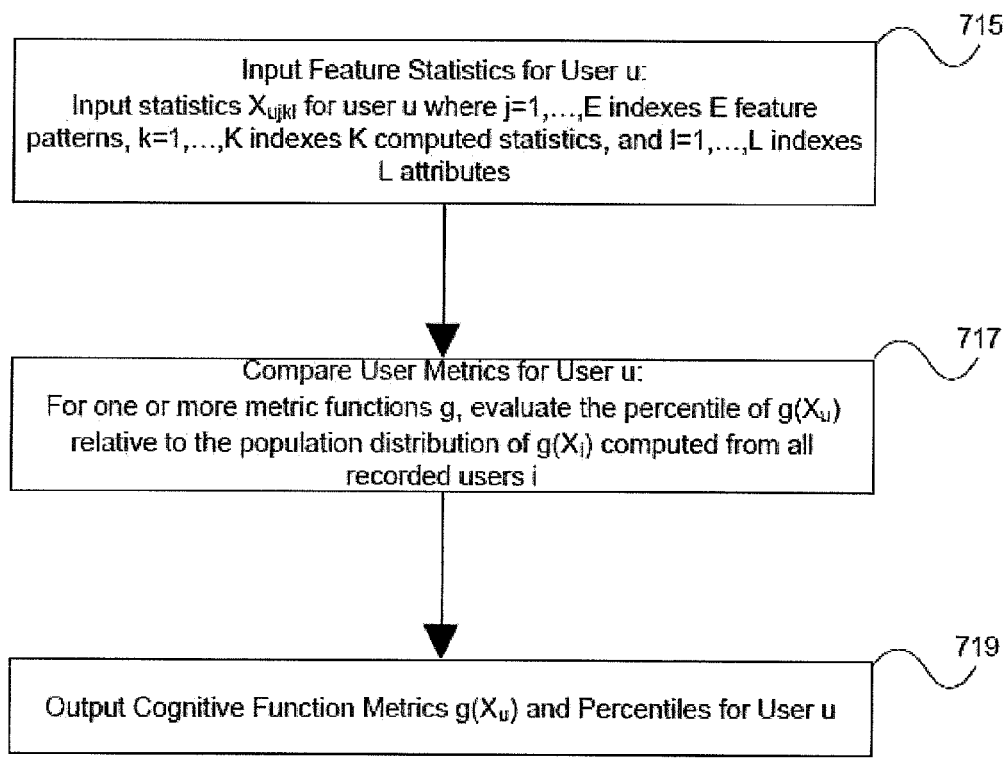

In addition to predicting scores of standard cognitive function tests, new cognitive function metrics may be computed from one or more metric functions in 717 of FIG. 7(c) using input feature statistics 715. The metric function g has the property that it maps the input feature statistics into a number. In 717, the cognitive function metric is computed from a user's feature statistics 715, a metric function g, and the metric function value's percentile rank relative to a population of users. The cognitive function metric and percentile is outputted in 719.

Figure 8:
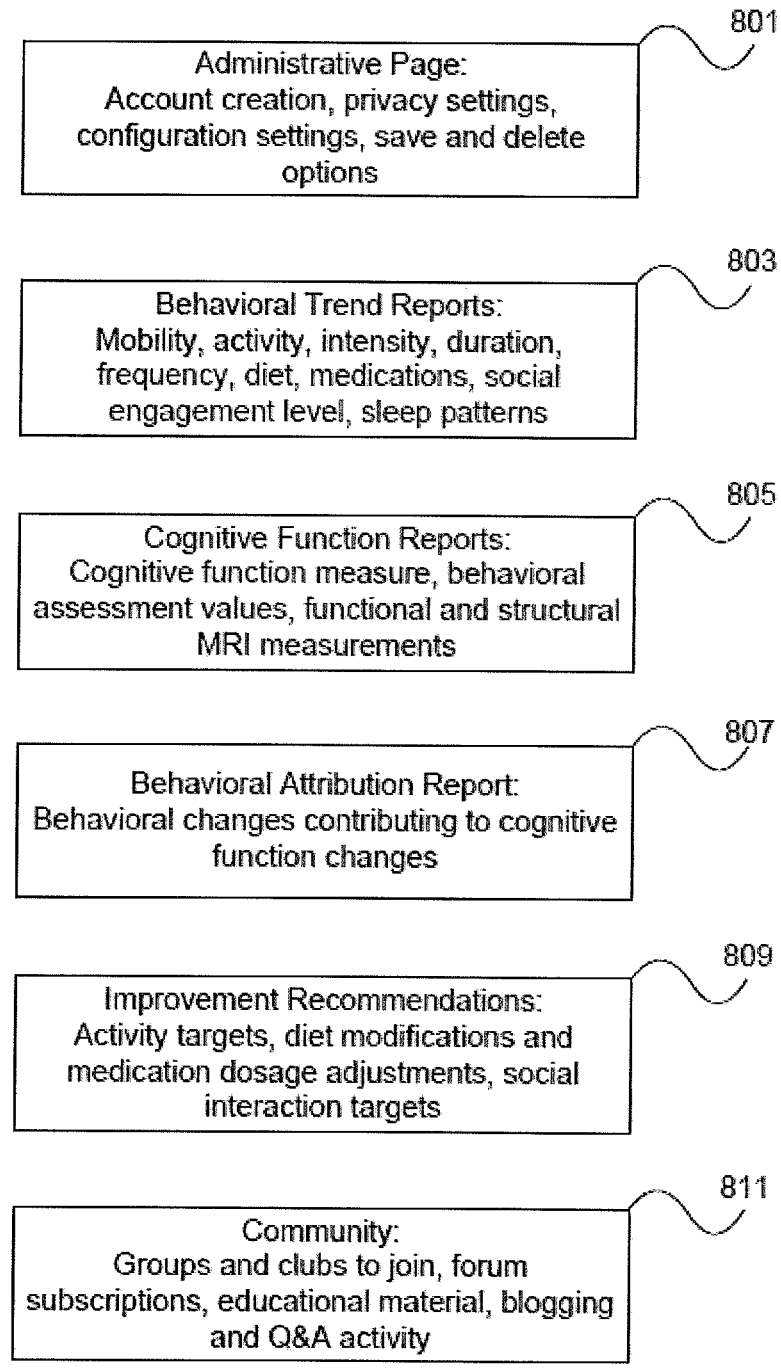
FIG. 8 is a reporting module in accordance with one embodiment of the present invention.

Referring to FIG. 8, a user may create and access an online account to obtain aggregated and detailed views of recorded data, cognitive function evaluation and target recommendations to improve cognitive function. In 801, a user may create an account and input personal demographic data and health data. The user also may set privacy levels, assign delegates to the account, or invite caregivers and physicians to participate. In 803, a user may access recent and historical views of aggregated recordings of (i) mobility, (ii) activity, (iii) social, (iv) learning, (v) diet, (vi) medications, (vii) applications used, (viii) electroencephalogram (EEG), and (ix) physiology, for example. A calendar widget (not illustrated) preferably enables the user to specify the aggregation period to use for the recent view and the historical views. Each group of recordings preferably offers granular views of behavior. Activity reports on physical activity and intensity, social engagement reports on outbound and inbound number of distinct people called, emailed, or text messaged, learning engagement reports on URLs visited and ebooks read, subject type and language, diet reports on food and beverages consumed and nutritional facts, applications reports on type of application, application name, duration and frequency of use, EEG reports on electroencephalogram recordings, and physiology reports on heart rate, pulse oxymetry, and body temperature preferably by time of day.

805 presents a time-series of the cognitive function evaluations computed by the metric computation module 700. If neuropsychological evaluations of cognitive function are available these may be overlaid on the time-series in 805. Functional measures using blood-oxygen level dependent (BOLD) functional magnetic resonance imaging (fMRI) and structural volume estimates using MRI of brain regions responsible for motivation, memory, learning that include by way of example the cingulate cortex, hippocampus, and entorhinal cortex, may be further overlaid on the time-series of 805.

The attribution report in 807 may compute the contribution of behavioral activity inferred from the recordings by the data collection module 400 to changes in cognitive function metrics. In 809, the attribution report may be used to set optimal target levels for mobility, physical, social, learning, diet, medications, and physiology to restore and improve cognitive function. To help the user achieve those targets, information is preferably provided in 811 to direct the user to relevant groups, forums, and educational material. The cycle then repeats itself.

After a target interval of one or two weeks has passed, new behavioral trend reports are preferably published in 803 and compared against the set targets, new values are computed for cognitive function and plotted in 805 to determine whether the target cognitive function was attained, new attributions are evaluated in 807 to explain observed changes in cognitive function, and new targets are set in 809.

An individual on any given day of the week uses his or her mobile device or other electronic device regularly as a common way of communicating to others, as a form of entertainment and as a means of retrieving and storing information. Therefore, the technology as disclosed and claimed herein does not require supervision over the individual users and in order to obtain meaningful information that is useful for measuring cognitive function and the individual does not have to change his/her lifestyle for the information to be gathered. For example, an individual may select an application on a mobile computer to launch the application by tapping on an icon displayed as part of the user interface where the user taps the touch-screen to open an application. The individual can launch an application such as a weather application to check the weather forecast, launch an email application to check email, scroll through emails and read and respond to some emails by keying in text with some typing errors and some misspellings. The user may get up for an early morning walk or run or bike ride and a combination of information may be captured by the global position function of the device as well as information or data from the gyroscopic motion sensor of the device indicative of the user exercising. When walking the user may trip or stumble quite often or their motion may not be fluid, which may be capture by the accelerometer and gyroscopic motion sensor as a sudden and violent movement. Also the user may actually trip and fall. The user may go for a drive over what appears to be a familiar route, but the GPS function captures what appears to be a series of incorrect turns. This may be indicative of a problem, although it may also be captured that the individual is also placing a call, on a call, or sending a text at the same time that the false or incorrect turn was made. The user may open a navigation application and enter a location search query and can use touch-screen gestures to scroll around on map within an application and select items on the map for additional feature information. When scrolling through the map, the individual can touch and swipe the map to follow highlighted directions or to search for a point of interest. Touches that dwell too long or swipes that are too short may result in an undesired response from the mobile computer. During the day, the individual may be traveling to and fro alone, but may need to reach out to their spouse, or son or daughter to coordinate a pick-up or meeting. The user can type text messages to selectively reach out. The individual may continue a text dialogue for a period of time. During the text dialogue the individual may have to back space several times to correct a typing error. The individual may want to meet with their spouse for dinner, but they do not know exactly were the restaurant of choice is located. The user can use the voice command feature to request directions and the GPS can be tracking the user's location, the user can request other content by keying in on a keyboard presented by the application or use voice commands to do the same, read and scroll through content, and the user can make calls or listen to messages. The user's activity is recorded on the device's persistent storage. The user makes or receives calls, email messages, and text messages. There can also be several days in a row where the user is carrying his/her electronic device, but out of the ordinary, the user may not place any call or send any text messages, browse their favorite social media application or visit their favorite website.

The date and time of each of the above activities, the activity duration, and the sender and recipient phone number or email address may be recorded in the device's persistent storage. The frequency of each event is preferably recorded, and the various qualitative characteristics of each event are also preferably recorded. The user may carry the mobile device with them while driving, using public transportation, walking, biking or running. While engaging in these activities, the electronic device's global positioning system (GPS) may record the user's longitude and latitude coordinates. Similarly, during those activities the device's acceleration and gyroscopic motion along a 3-coordinate system may be recorded. The type of locations that the individual traveled may be determined and the characteristic of the motion of the user may also be evaluated for fluidity or erratic motion. This information is preferably recorded in the device's persistent storage. When a user browses URLs on an internet browser application resident on the electronic device, or reads an e-book on an e-book reader resident on the mobile device, the URLs browsed and the pages of the e-book read, the start time and end time between URLs and pages are preferably recorded by the system and method of this invention and persisted in the device's persistent storage.

Note that gesture, tapping, body motion and eye movement activity, typing activity, and voice command activity during the use of applications is preferably captured separately in and recorded with the time and application in which that activity took place. In this way, the system tracks gestures used during browsing, paging and scrolling, for example. Lastly, a bar code scanning application and medical reminder application resident on the electronic device may enable the user to scan grocery purchases, and meals and beverages purchased when the latter have bar codes and to keep track of medications taken, dosage and frequencies. The bar code scanning application preferably has access to a database of nutritional facts. If a nutritional fact for the scanned bar code is not in the database, then the application may instruct the user to photograph the nutritional fact label of the item. The bar code information and medications taken, dosages and frequencies are preferably persisted in the device's persistent storage.

The data captured in the device's persistent storage may be transmitted to cloud computers. Transmission may use a secure channel and use hypertext transfer protocol secure (HTTPS) to securely transfer the data. The cloud computers may analyze the recorded data against historical recordings and against recordings averaged over other users demographically matched to the existing user. The output of the analysis is preferably an evaluation of cognitive function and the attribution to changes in behavioral activities inferred from the activities recorded including social engagement, physical activity, learning activity, and diet. The user may log into his or her personal password protected online account to view the results of the analysis together with suggestions for improvement.

Various recordings of data representative of the quantity and quality of interactions and occurrences of events using the mobile computing device may be made. The data may be encoded with representative tags.

A description of the type of encoded data with representative log semantics when an application is launched on the electronic device may be as follows:

| App Log | Description |
| --- | --- |
| app_pkg_name | Application launched |
| app_start_time | Start date and time of use |
| app_end_time | End date and time of use |

A description of the type of encoded data with representative log semantics following incoming, outgoing and missed calls on the electronic device may be as follows:

| Call Log | Description |
| --- | --- |
| call_type | Values (1, 2, 3) meaning (incoming, outgoing, missed) |
| phone_number | Phone number of call |
| call_start_time | Start date and time of call |
| call_end_time | End date and time of call |
| audio_recording_file | File name of recorded call and null if not recorded |

A description of the type of encoded data with representative log semantics following gestures made on the touchscreen of the electronic device during use of an application may be as follows:

| Gesture Log | Description |
| --- | --- |
| app_pkg_name | Application in use |
| view_name_in_pkg | Package within application (eg. Contacts or missed calls, in phone application) |
| scroll_unit | Values (1, 2) meaning (items, pixels) |
| item_count | Number of scrollable items |
| from_idx | Index of first item visible when scrolling |
| to_idx | Index of last item visible when scrolling |
| scroll_direction | Values (1, 2) meaning scroll in (X, Y) direction |
| max_scroll | Max_scroll x dir (or y dir): gives the max scroll offset of the source left edge (or top edge) in pixels |
| scroll_value | Scroll_value X dir (or Y dir): gives the scroll offset of the source left edge (or top edge) in pixels |
| timestamp | Date and time |

A description of the type of encoded GPS data with representative log semantics on the electronic device may be as follows:

| GPS Log | Description |
| --- | --- |
| latitude | Latitude of current location |
| longitude | Longitude of current location |
| altitude | Altitude of current location |
| bearing | Horizontal direction of travel in degrees (0.0, 360.0] |
| speed | Travel speed in meters per second |
| accuracy | Radius in meters of 68% confidence circle |
| timestamp | Date and time |

A description of the type of encoded data with representative log semantics when the keyboard is used on the electronic device may be as follows:

| Key Log | Description |
| --- | --- |
| session_id | Identifies each session |
| key_type | Values (1, 2) meaning (alphanumeric, control key) |

-continued

| Key Log | Description |
| --- | --- |
| key_code | Ascii code of pressed key |
| key_desc | Either the alphanumeric value or a control descriptor |
| key_press_time | Date and time in milliseconds when key is pressed |
| key_release_time | Date and time in milliseconds when key is released |
| key_press_duration | Duration of key press in milliseconds |

A description of the type of encoded sensor data with representative log semantics on a mobile electronic may be as follows:

| Sensor Log | Description |
| --- | --- |
| sensor_type | Values (1, 2) meaning (accelerometer, gyroscope) |
| value_0 | Value of first coordinate measurement |
| value_1 | Value of second coordinate measurement |
| value_2 | Value of third coordinate measurement |
| timestamp | Date and time of coordinate measurements |

A description of the type of encoded data with representative log semantics when text messages are sent or received on the electronic device may be as follows:

| SMS Log | Description |
| --- | --- |
| sms_type | Values (1, 2) meaning (Incoming, Outgoing) |
| phone_number | Phone number of message |
| message | Message text |
| timestamp | Date and time of message |

A description of the type of encoded data with representative log semantics when URLs are browsed on the electronic device may be as follows:

| URL Log | Description |
| --- | --- |
| URL | URL viewed |
| timestamp | Start date and time of URL view |

In one implementation of the method and system, in order to establish a baseline of data, supervised benchmark testing may be conducted on an initial test group of individuals where these individuals take a neuropsychological benchmark test for cognitive function, and the data may be stored. Each of the same individuals who are tested may be provided with electronic devices having the computer program for performing the system and method. Data for each individual may be recorded as outlined herein and the data from the electronic device usage may be correlated to the benchmark testing results and cognitive function. Cognitive function levels and bands may also be determined from the result. Once certain baselines have been established and correlations are made between cognitive function and electronic device usage, subsequent electronic device usage by individuals may be utilized to improve the system and method as learning occurs. The learning from the subsequent electronic device usage may be considered unsupervised learning.

The cognitive function module may access the recordings made by the data collection module and transmitted to cloud computers. Patterns in a user's interactions with an electronic device captured are preferably analyzed for changes in cognitive function. The above described activity for an individual and his interface with a electronic computing device may be captured and utilize. Changes in applications opened and closed by a user, frequency and latencies between opening and closing, and their diurnal and weekly variations may be inputs to the feature extraction module and the learning, and computation of cognitive function by the metric computation module. Changes in a user's gestures, tapping, body motions, and eye movements used as inputs to applications such as type of gesture, gesture durations, including false positive gestures of excessive scrolling during search and excessive paging during browsing, may be additional inputs to the feature extraction module and the learning, and computation by the metric computation module. Changes in a user's kinetic activities of motion, gait and balance recorded from wearable gyroscopic and accelerometer sensors, may further be additional inputs to the feature extraction module and the learning, and computation by the metric computation module.

Similarly, when the above described individual makes character inputs, recurring spelling mistakes, omissions, excessive backspace corrections, irregular latency variances in common words, length of messages, and message coherence may all be inputs into the feature extraction, learning, and computation of cognitive function. Signal processing of speech and voice may provide additional input to the computation including emerging irregularities in phones and phoneme latencies, and narrowing or shifting of the voice frequency spectrum. The time of day and day of week may be captured in the recordings of and used by the cognitive function computation to adjust, or explain variances that can be attributed to individual fatigue and other factors that may have short-term effects on cognitive function.

Further, to correct for motion artifact such as from driving or walking, GPS, gyroscope and accelerometer recordings made are preferably used as additional inputs in the feature extraction, learning and computation of cognitive function. To correct for physiologic effects such as anxiety, general malaise, illness, the physiologic measurements of heart-rate, blood pressure, blood glucose, blood oxymetry, and body temperature when available and recorded may be used as further inputs to the evaluation of cognitive function. Behavioral activities recorded on the electronic device may be analyzed to explain changes in the cognitive function that is computed using inputs. A user's incoming and outgoing email, phone calls, and text messages, their frequencies and length may also be used as a proxy for the user's level of social engagement. A user's daily travel, the inferred mode of travel including vehicle, bicycle, foot or other, the user's sleep and rest patterns inferred by electronic device "quiet" times, may be used to infer physical activity. When this data is available and when correlated with physical activity data such as rapid heart rates from anxiety or illness may be distinguished from exercise induced changes, improving the inference of physical activity and quantifying the intensity of that activity. Analysis of patterns in groceries purchased, food and drinks consumed provides a proxy to nutritional intake may also be made. Analysis of changes in medications taken, dosages and frequencies including missed medications, changes in dosage and new medications that may alter mental state are preferably used to infer their effect on the user's cognitive function.

The various implementations and examples shown above illustrate a method and system for assessing cognitive function using an electronic computing device. A user of the present method and system may choose any of the above implementations, or an equivalent thereof, depending upon the desired application. In this regard, it is recognized that various forms of the subject method and system could be utilized without departing from the spirit and scope of the present implementation.

As is evident from the foregoing description, certain aspects of the present implementation are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present implementation. Accordingly, the specification and drawings are to be regarded in an illustrative rather than a restrictive sense.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different implementations of which there are many possible permutations.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a smart phone, a web appliance, a network router, switch or bridge, or any machine capable of executing a set of instructions (sequential or otherwise) that specify actions to be taken by that machine or computing device. Further, while only a single machine is illustrated, the term "machine" shall also be taken to include any collection of machines that individually or jointly execute a set (or multiple sets) of instructions to perform any one or more of the methodologies discussed herein.

The example computer system and client computers include a processor (e.g., a central processing unit (CPU) a graphics processing unit (GPU) or both), a main memory and a static memory, which communicate with each other via a bus. The computer system may further include a video/graphical display unit (e.g., a liquid crystal display (LCD) or a cathode ray tube (CRT)). The computer system and client computing devices also include an alphanumeric input device (e.g., a keyboard or touch-screen), a cursor control device (e.g., a mouse or gestures on a touch-screen), a drive unit, a signal generation device (e.g., a speaker and microphone) and a network interface device.

The drive unit includes a computer-readable medium on which is stored one or more sets of instructions (e.g., software) embodying any one or more of the methodologies or systems described herein. The software may also reside, completely or at least partially, within the main memory and/or within the processor during execution thereof by the computer system, the main memory and the processor also constituting computer-readable media. The software may further be transmitted or received over a network via the network interface device.

The term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present implementation. The term "computer-readable medium" shall accordingly be taken to include, but not be limited to, solid-state memories, and optical media, and magnetic media.

I claim:

1. A computer-implemented method for assessing brain health of a person, the method comprising the steps of:
   a. recording, separately and unobtrusively at a data collection module installed at one or more electronic computing devices, inputs associated with one or more interactions of the person with said one or more electronic computing devices;
   b. transmitting said inputs from said data collection module installed at the one or more electronic computing devices to a computing system comprising a processor executing a learning function mapping;
   c. computing, by said computing system, a brain health metric by performing said learning function mapping from said inputs to said brain health metric, wherein said brain health metric is a neuropsychological test; and
   d. outputting, by said computing system, said brain health metric.

2. The method of claim 1, wherein the one or more interactions includes at least one of: applications opened, inputs typed, gesture patterns used on a touch screen, body motions, eye movements, and voice input.

3. The method of claim 1, wherein the one or more electronic devices includes at least one of: a smart phone, a tablet computer, a wearable electronic device, and a household electronic device.

4. The method of claim 2, where to quantify the effect of social interaction, mobility, physiology, cognitive stimulation, diet, medication taken and traumatic exposure on a person's brain health, said method further comprises the steps of:
   a. recording at said one or more electronic computing devices inputs associated with a measurement of one of social interaction, mobility, physiology, cognitive stimulation, diet, medication taken and traumatic exposure;
   b. performing a learning function mapping from said inputs associated with the measurement to said brain health metric; and
   c. outputting an attribution to said brain health metric that is explained by said inputs associated with the measurement.

5. The computer implemented method of claim 4, wherein the social interaction measurement is one of length, duration, frequency, volume, sentiment, and mood associated with one of an incoming call, an outgoing call, a text, and an email message.

6. The computer implemented method of claim 4, wherein the social interaction measurement is a measurement from one of an email, phone, texting, or other communication application on said one or more electronic computing devices.

7. The computer implemented method of claim 4, wherein the mobility measurement is one of intensity, duration, and frequency of locomotor activity.

8. The computer implemented method of claim 4, wherein the mobility measurement is a measurement from one of an accelerometer application and a gyroscope application on said one or more electronic computing devices.

9. The computer implemented method of claim 4, wherein the physiology measurement is one of a heart rate, a blood pressure, a blood oxymetry, a blood glucose, a body temperature, a body fat, a body weight, a sleep duration and quality, and an electroencephalogram.

10. The computer implemented method of claim 4, wherein the cognitive stimulation measurement is one of URLs visited, books and articles read, and games played on said one or more electronic computing devices.

11. The computer implemented method of claim 4, wherein the cognitive stimulation measurement is one of a setting of, or a recording from, a brain stimulation device.

12. The computer implemented method of claim 4, wherein the diet measurement is one of a caloric intake, a nutritional value, a food type, and alcohol, caffeine, drug, and vitamin consumption.

13. The computer implemented method of claim 4, wherein the medication measurement is one of a dosage, a frequency, and a duration of a medication.

14. The computer implemented method of claim 4, wherein the traumatic exposure measurement is one of a date and a severity of an incident.

15. A computer-readable medium comprising instructions that when executed by a processor perform a method for assessing brain health of a person, the method comprising the following steps:
   a. recording, separately and unobtrusively at a data collection module installed at one or more electronic computing devices, inputs associated with one or more interactions of the person with said one or more electronic computing devices;
   b. transmitting said inputs from said data collection module installed at the one or more electronic computing devices to a computing system executing a learning function mapping;
   c. computing, by said computing system, a brain health metric by performing said learning function mapping from said inputs to said brain health metric, wherein said brain health metric is a neuropsychological test; and
   d. outputting, by said computing system, said brain health metric.

16. The computer-readable medium of claim 15, wherein the one or more interactions includes at least one of: applications opened, inputs typed, gesture patterns used on a touch screen, body motions, eye movements, and voice input.

17. The computer-readable medium of claim 15, wherein the one or more electronic devices includes at least one of: a smart phone, a tablet computer, a wearable electronic device, and a household electronic device.

18. The computer-readable medium of claim 17, where to quantify an effect of social interaction, mobility, physiology, cognitive stimulation, diet, medication taken and traumatic exposure on a person's brain health, said instructions that when executed by a processor further comprise the steps of:
   a. recording at said one or more electronic computing devices inputs associated with a measurement of one of social interaction, mobility, physiology, cognitive stimulation, diet, medication taken and traumatic exposure;
   b. performing a learning function mapping from said inputs associated with the measurement to said brain health metric; and
   c. outputting an attribution to said brain health metric that is explained by said inputs associated with the measurement.

19. A computer-implemented system for assessing brain health of a person, the system comprising:
   a. one or more electronic computing devices:
   recording, separately and unobtrusively at a data collection module, inputs associated with one or more interactions of the person with said one or more electronic computing devices; and
   transmitting said inputs from said data collection module installed at the one or more electronic computing devices to a computing system comprising a processor executing a learning function mapping;
   b. said computing system:
   computing a brain health metric by performing said learning function mapping from said inputs to said brain health metric, wherein said brain health metric is a neuropsychological test; and
   outputting said brain health metric.

* * * * *